United States Patent
Fu et al.

(10) Patent No.: US 9,670,224 B2
(45) Date of Patent: Jun. 6, 2017

(54) FORSYTHIASIDE SULFATE AND DERIVATIVES THEREOF, PREPARATION METHOD AND APPLICATION THEREOF

(71) Applicant: Li Fu, Dalian (CN)

(72) Inventors: Li Fu, Dalian (CN); Hongyu Fan, Dalian (CN); Shuo Wang, Dalian (CN)

(73) Assignee: Li Fu, Dalian (CN)

( * ) Notice: Subject to any disclaimer, the term of this patent is extended or adjusted under 35 U.S.C. 154(b) by 0 days.

(21) Appl. No.: 15/036,613

(22) PCT Filed: Nov. 6, 2014

(86) PCT No.: PCT/CN2014/090465
§ 371 (c)(1),
(2) Date: May 13, 2016

(87) PCT Pub. No.: WO2015/070724
PCT Pub. Date: May 21, 2015

(65) Prior Publication Data
US 2016/0355524 A1    Dec. 8, 2016

(30) Foreign Application Priority Data
Nov. 18, 2013    (CN) .......................... 2013 1 0580801

(51) Int. Cl.
*C07D 493/00* (2006.01)
*C07D 493/04* (2006.01)

(52) U.S. Cl.
CPC .................. *C07D 493/04* (2013.01)

(58) Field of Classification Search
CPC .................................................. C07D 493/04
USPC .......................................................... 549/464
See application file for complete search history.

(56) References Cited

FOREIGN PATENT DOCUMENTS

| CN | 101537046 | 9/2009 |
|----|-----------|--------|
| CN | 101974047 | 2/2011 |

OTHER PUBLICATIONS

International Search Report for International application No. PCT/CN2014/090465, date of mailing Feb. 10, 2015.
Niu, Xusheng et al., "Studies on the antivirus activity and chemical constituents from Shuanghuanglian Injection powder", Modern Chinese Medicine, No. 1, vol. 8, Jan. 31, 2006 (Jan. 31, 2006). see pp. 16-18 and 27. especially compound IV.
Rahman, M.M.A. et al., "Lignans of Forsythia intermedia", Phytochemistry, No. 6, vol. 29, Dec. 31, 1990 (Dec. 31, 1990), see pp. 1971-1980.

*Primary Examiner* — T. Victor Oh
(74) *Attorney, Agent, or Firm* — Greer, Burns & Crain, Ltd.

(57) ABSTRACT

The present invention provides a forsythiaside sulfate derivatives as represented by the following formula, the preparation method and antiviral application thereof:

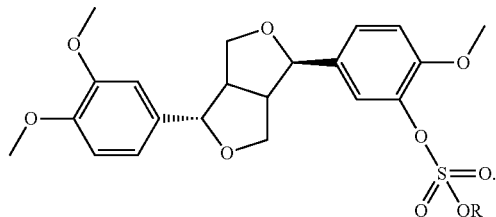

10 Claims, 2 Drawing Sheets

FORSYTHIASIDE SULFATE AND DERIVATIVES THEREOF, PREPARATION METHOD AND APPLICATION THEREOF

This application is a U.S. National Phase under 35 U.S.C. §371 of International Application No. PCT/CN2014/090465, filed Nov. 6, 2014, which claims priority under 35 U.S.C. §§119 and 365 to Chinese Application No. 201310580801.5, filed Nov. 18, 2013.

TECHNICAL FIELD

The present invention belongs to the field of medicinal chemistry, and in particular relates to forsythiaside sulfate derivatives and a preparation method thereof, as well as pharmacological effects of such derivatives in terms of viral resistance.

BACKGROUND ART

Forsythiaside, as an aglycon part of forsythin, is also known as phillygenin, is a main active component of *Forsythia suspensa* of the genus *Forsythia* in, the family Oleaceae and has a structure as represented below. Modern pharmacological researches show that forsythiaside has antiviral, antioxidant, lowering blood lipid scavenging free radical, antibacterial, antitumor, anti-inflammatory effect and the like.

Forsythiaside has unstable molecules which is prone to oxidized and easy to change the configuration in an acidic environment. Researches simulating forsythin metabolism through rat enteric bacteria discover that forsythin is easily metabolized by intestinal flora into a new metabolite.

Researches on metabolism of phenolic structural drugs discover that drugs with the structural of phenolic hydroxylare easily metabolized by in-vivo sulfatases into phenol sulfate derivatives and have good activity. For example, daidzein sulfate derivatives, edaravone sulfate derivatives, genistein sulfate derivatives, resveratrol sulfate derivatives and the like. Therefore, we designed sulfate derivatives of phillygenin and carried out chemical synthesis and pharmacological studies.

SUMMARY OF THE INVENTION

The technical problem to be solved by the present invention is to prepare forsythiaside sulfate derivatives by chemical synthetic method. The present invention provides forsythiaside sulfate derivatives. In addition, the present invention also provides a method for preparing forsythiaside sulfate derivatives, and is suitable for industrial scale-up production. First, the present invention provides a forsythiaside sulfate and its derivatives as represented by the following formula:

wherein R is H, $Na^+$, $K^+$, $NH_4^+$, tetramethyl ammonium, tetraethyl ammonium, methylamino, dimethylamino, trimethylamino, triethylamino, diethylamino, ethylamino, ethanolamino, diethanolarnino, piperidyl, piperazinyl or pyrazinyl.

Secondly, the present invention provides a pharmaceutical composition, which comprises the forsythiaside sulfate derivatives of the present invention and pharmaceutically acceptable excipients.

Herein, the pharmaceutically acceptable excipients refer to non-toxic solid, semi-solid or liquid fillers, diluents, carriers, pH regulators, ionic strength regulators, slow-release or controlled-release agent, wrapping material or other pharmaceutical excipients. The used carrier may be adapted to corresponding drug administration mode, can use the excipients which are well known to those skilled in the art to formulated into injections, freeze-dried powder (for injection), sprays, oral solutions, oral suspensions, tablets, capsules, enteric tablets, pills, powders, granules, sustained-release or delayed-release preparations and the like. The forsythiaside sulfate derivatives of the first aspect of the present invention are preferred and administered by injection or through digestive tract, therefore the pharmaceutical composition of the present invention is preferably injections or preparations administered through digestive tract, i.e., the auxiliary materials suitable for being formulated into injections or preparations administered through digestive tract are particularly preferred, wherein "administration through digestive tract" refers herein to an approach of administrating drug preparations through the digestive tracts of patients, comprising oral administration, intragastric administration, enema administration and the like, preferably oral administration, for example, excipients which are well known to those skilled in the art can be used to formulate into oral solutions, oral suspensions, tablets, capsules, enteric tablets, pills, powders, granules, sustained-release or delayed-release preparations and the like; wherein the injection preparations are mainly injections and powder-injections, Thirdly, the present invention provides a preparation method of forsythiaside sulfate and its derivatives, comprising the following sequentially performed steps:

1) dissolving forsythiaside in the organic solvent to obtain a forsytitiaside solution;

2) first, adding a sulfating agent into the forsythiaside solution and mixing well; and then, carrying out esterification reaction to obtain a product mixture liquid;

3) adding a base to adjust the pH value of the mixture liquid to 8-10;

4) separating and, purifying the mixture liquid to obtain the final product.

Wherein the organic solvent in step 1) is selected from one of pyridine, N,N-climethylniethylformarnide, N,N-dimethylacetamide or dichloromethane.

Wherein the sulfating agent is added to the forsythiaside solution at 0-5° C.

In particular, the sulfating agent is added to the forsythiaside solution at 0° C., and stirred uniformly.

In particular, the sulfating agent is selected from a chlorosulfonic acid, a sulfur trioxide-triethylamine complex, a sulfur trioxide-pyridine complex or a sulfur trioxide-trimethylamine complex, and preferably the chlorosulfonic acid.

In particular, the molar ratio of the forsythiaside in the forsythiaside solution to the sulfating agent is 1:1-10, and preferably 1:2.

Wherein the temperature of the esterification reaction in step 2) is 0-110° C.

In particular, the reaction temperature of the lesterifcation reaction performed on the forsythiaside and chlorosulfonic acid is 0-10° C., and preferably 10° C.; the reaction temperature of the esterification reaction performed on the forsythiaside and the sulfur trioxide-triethylamine complex, the sulfur trioxide-pyridine complex or the sulfur trioxide-trimethylamine complex is 100-110° C.

In particular, after the esterification reaction performed on the forsythiaside and the sulfur trioxide-triethylamine complex, the sulfur trioxide-pyridine complex or the sulfur trioxide-trimethylamine complex, the method further includes cooling the mixture of the esterification reaction, and then adding a base to adjust the pH value of the mixture to 8-10. Particularly, the mixture of the esterification reaction is cooled to the room temperature (10-30° C.). Wherein the pH value in step 3) is preferably 10; the base is selected from an organic base or an inorganic base.

In particular, the inorganic base is selected from one of sodium carbonate, potassium carbonate, sodium bicarbonate, potassium bicarbonate, sodium hydroxide, potassium hydroxide or aqueous ammonia, and preferably sodium hydroxide, potassium hydroxide solution or aqueous ammonia; the organic base is selected from tetrametivi ammonium, tetraethyl ammonium, methyl amine, dimethyl amine, trimethyl amine, triethyl amine, diethyl amine, ethyl amine, ethanol amine, diethanol amine, piperidine, piperazine or pyrazine.

Wherein the product mixture liquid is separated by using silica gel column chromatography in step 4).

In particular, the silica gel chooses GF254 silica gel.

In another aspect, the present invention provides an application of the forsythiaside sulfate and its derivatives in preparation of anti-viral drugs.

Wherein the anti-viral drugs are selected from anti-influenza drugs, anti-parainfluenza drugs, anti-respiratory syncytial virus drugs, anti-herpes simplex virus type-I drugs, and anti-coxsackievirus A 16 drugs.

In still another aspect, the present invention provides an antiviral drug containing forsythiaside sulfate or forsythiaside sulfate derivatives.

The advantages of the present invention are as follows: the preparation method of forsythiaside sulfate derivatives of the present invention is easy to control, is high in comprehensive yield of product, and is suitable for industrial mass production; the forsythiaside sulfate derivatives of the present invention have significant antiviral effect, and the inhibition efficacy to virus reaches more than 80%; results of in-vivo antiviral tests show that the forsythiaside sulfate derivatives have relatively significant inhibition effects on influenza virus and parainfluenza virus as well as the mice viral pneumonia caused thereby, can significantly reduce pulmonary index and hemagglutination titer, and also make significant improvements in pulmonary histopathology.

DETAILED DESCRIPTION OF THE INVENTION

The present invention is further described through the following embodiments. However, these embodiments are only meant for illustration, and should not be construed as any limitation to the scope of the present invention. In addition, the reagents and raw materials in the embodiments can all be commercially available, if not mentioned, reference may be made to organic synthesis guide, guideline of drug regulatory administration and corresponding manufacturers' instructions to equipments and reagents and so on.

Embodiment 1

1, Forsythiaside (4 g, 10.75 mmol) is added into 180 ml of dried anhydrous pyridine, and stirring is carried out for dissolving, to obtain a forsythiaside solution;

2, Under the condition of an ice bath, dichlorornethane solution of chiorosulfonic acid (1.4 ml, about 21.5 mmol) is dropwise added into the forsylltiaside solution, stirring is performed at the same time, and the speed of dropwise addition is 1 drop (about 50 μl/drop)/2 s. i.e., the molar ratio of the forsythiaside to the chlorosulfonic acid in the present embodiment is 1:2.

3, After completion of the dropwise addition, under a stirring condition, temperature is raised and maintained at 10° C., and esterification reaction is carried out;

4, Under the condition of maintaining temperature at 10° C., esterification reaction is completed, upon reaction for 1 h, methanol solution (5 ml) of sodium hydroxide is added to adjust the pH value to 10, the reaction mixture is subsequently distilled with a reduced pressure to remove solvent, then, sample is loaded on GF254 silica gel column chromatography, the eluent is a mixture liquid of chloroform and methanol, wherein the volumetric ratio of the chloroform to the methanol is 9:1. A forsythiaside sodium sulfate (compound 1) is obtained by means of silica gel column chromatography.

The forsythiaside sodium sulfate (3 g) is a white solid, which is soluble in water and ethanol. After being spread on a TLC plate (with the chromatographic solution being chloroform/methanol 10:1, and Rf being 0.4), it shows a purple-red color by spraying 10% of $H_2SO_4$-ethanol reagent. In an ESI-MS spectrum, m/z[M-Na]$^-$ is 451, molecular weight is 474.

The $^1$H-NMR (600 MHz, $d_6$-DMSO) of compound 1 is as follows:

δ (ppm):7.4 (1H, d, J=8.4 Hz, H—), 6.9 (5H, m, Ar—H), 4.8 (1H, d, J=4.8 Hz, H-6), 4.38 (H, d, J=6.6 Hz, H-8), 4.10 (1H, d, J=9.0 Hz, H-2), 3.75 (12H, d, J=8.4 Hz, H-8,4, O—CH3), 3.11 (1H, t, J=8,1 Hz, H-5), 2.85 (1H, d, J=7.2 Hz, H-1);

The $^{13}$C-NMR (150 MHz, $d_6$-DMSO) of compound 1 is as follows:

δ (ppm):150.99 (C-3"), 148.97 (C-3'), 148.10 (C-4"), 142.51 (C-4'), 137.20 (C-1"), 131.73 (C-1'), 121.33 (C-5'), 118.09 (C-6'), 118.06 (C-6"), 112.09 (C-5"), 110.94 (C-2'), 110.00 (C-2"), 87.22 (C-2), 81.76 (C-6), 70.87 (C-8), 69.44 (C-4), 56.23 (C—OCH3), 55.99 (C—OCH3), 54.54 (C—OCH3), 53.37 (C-1), 49.78 (C-5) ppm According to the testing data of ESI-MS, $^1$H-NMR and $^{13}$C-NMR, it is determined that the molecular formula of compound 1 is: $C_{21}H_{23}O_9SNa$, and the structural formula is:

Embodiment 2

1. Forsythiaside (4 g, 10.75 op is added into 180 ml of dried anhydrous pyridine, and stirring is carried out for dissolving, to obtain a forsythiaside solution;

2, Under the condition of an ice bath, dichloromethane solution of chlorosulfonic acid (1.4 ml, about 21.5 mmol) is dropwise added into the forsythiaside solution; stirring is performed at the same time, and the speed of the dropwise addition is 1 drop (about 50 μl/drop)/2 s, i.e., the molar ratio of the forsythiaside to the chlorosulfonic acid in the present embodiment is 1:2.

3, After completion of the dropwise addition, under a stirring condition, temperature is raised and maintained at 10° C., and esterification reaction is carried out;

4, Under the condition of maintaining temperature at 10° C., esterification reaction is completed, upon reaction for 1 h, methanol solution (5 ml) of potassium hydroxide is added to adjust the pH value to 10, the reaction mixture is subsequently distilled with a reduced pressure to remove solvent, then, sample is loaded on GE254 silica gel column chromatography, the eluent is a mixture liquid of chloroform and methanol, wherein the volumetric ratio of the chloroform to the methanol is 9:1, A forsythiaside potassium sulfate (compound 2) is obtained by means of silica gel column chromatography.

The Forsythiaside potassium sulfate (3 g) is a white solid, which is soluble in water and ethanol. After being spread on a TLC plate (with the chromatographic solution being chloroform/methanol 10:1, and Rf being 0.4), it shows a purple-red color by spraying 10% of $H_2SO_4$-ethanol reagent, In ESI-MS spectrum, $m/z[M-K]^-$ is 451, and the molecular weight is 490.

The $^1H$-NMR (600 MHz, $d_6$-DMSO) of compound 2 is as follows:

δ (ppm):7.4 (1H, d, J=8.4 Hz, H—), 6.9 (5H, m, Ar—H), 4.8 (1H, d, J=4.8 Hz, H-6), 4.38 (H, d, J=6.6 Hz, H-8), 4.10 (1H, d, J=9.0 Hz, H-2), 3.75 (12H, d, J=8.4 Hz, H-8,4, O—$CH_3$), 3.10 (1H, t, J=8.1 Hz, H-5), 2.84 (1H, d, J=7.2 Hz, H-1);

The $^{13}C$-NMR (125 MHz, $d_6$-DMSO) of compound 2 is as follows:

δ (ppm):150.99 (C-3"), 148.97 (C-3'), 148.10 (C-4"), 142.51 (C-4'), 137.20 (C-1"), 131.73 (C-1'), 121.33 (C-5'), 118.09 (C-6'), 118.06 (C-6"), 112.09 (C-5"), 110.95 (C-2'), 110.00 (C-2"), 87.23 (C-2), 81.76 (C-6), 70.87 (C-8), 69.44 (C-4), 56.21 (C—$OCH_3$), 55.99 (C—$OCH_3$), 54.52 (C—$OCH_3$), 53.37 (C-1), 49.78 (C-5) ppm.

According to the testing data of ESI-MS, $^1H$-NMR and $^{13}C$-NMR, it is determined that the molecular formula of compound 2 is: $C_{21}H_{23}O_9SK$; and the structural formula is:

Embodiment 3

1, Forsythiaside (4 g, 10.75 mmol) is added into into 180 ml of dried anhydrous pyridine, and stirring is carried out for dissolving, to obtain a forsythiaside solution;

2 Under the condition of an ice bath, a dichloromethane solution of chlorosulfonic acid (1.4 ml, about 21.5 mmol) is dropwise added into the forsythiaside solution; stirring is performed at the same time, and the speed of the dropwise addition is 1 drop (about 50 μl/drop)/2 s, i.e., the molar ratio of the forsythiaside to the chlorosulfonic acid in the present embodiment is 1:2.

3, After completion of the dropwise addition, under a stirring condition, temperature is raised and maintained at 10° C., and esterification reaction is carried out;

4, Under the condition of maintaining temperature at 10° C., esterification reaction is completed, upon reaction for 1 h, ammonia water (5 ml) is added to adjust the pH value to 8, the reaction mixture is subsequently distilled with a reduced pressure to remove solvent, then, sample is loaded on GF254 silica gel column chromatography, the eluent is a mixture liquid of chloroform and methanol, wherein the volumetric ratio of the chloroform to the methanol is 9:1, A forsythiaside ammonium sulfate (compound 3) is obtained by means of silica gel column chromatography. Forsythiaside ammonium sulfate (3 g) is a white solid, which is soluble in water and ethanol. After being spread on a TLC plate (with the chromatographic solution being chloroform/methanol 10:1, and Rf being 0.4), it shows a purple-red color by spraying 10% of $H_2SO_4$-ethanol reagent. In ESI-MS spectrum, $m/z[M-NH_4]^-$ is 451, and the molecular weight is 469.

The $^1H$-NMR (600 MHz, $d_6$-DMSO) of compound 3 is as follows:

δ (ppm):7.4 (1H, d, J=8.4 Hz, H—), 6.9 (5H, m, Ar—H), 4.8 (1H, d, J=4.8 Hz, H-6), 4.38 (H, d, J=6.6 Hz, H-8), 4.10 (1H, d, J=9.0 Hz, H-2), 3.75 (12H, d, J=8.4 Hz, H=8,4, O—$CH_3$), 3.12 (1H, t, J=8.1 Hz, H-5), 2.86 (1H, d, J=7.2 Hz, H-1); The $^{13}C$-NMR (125 MHz, $d_6$-DMSO) of compound 3 is as follows:

δ (ppm):150.99 (C-3"), 148.97 (C-3'), 148.10 (C-4"), 142.51 (C-4'), 137.20 (C-1"), 131.73 (C-1'), 121.32 (C-5'), 118.09 (C-6'), 118.06 (C-6"), 112.09 (C-5"), 110.94 (C-2'), 110.00 (C-2"), 87.22 (C-2), 81.76 (C-6), 70.87 (C-8), 69.44 (C-4), 56.21 (C—$OCH_3$), 55.99 (C—$OCH_3$), 54.52 (C—$OCH_3$), 53.37 (C-1), 49.78 (C-5) ppm.

According to the testing data of ESI-MS, $^1H$-NMR and $^{13}C$-NMR, it is determined that the molecular formula of compound 3 is: $C_{21}H_{27}NO_9S$; and the structural formula is:

Embodiment 4

1. Forsythiaside (4 g, 10.75 mmol) is added into 180 ml of dried anhydrous N,N-dimethylformamide, and stirring is carried out for dissolving, to obtain a forsythiaside solution;

2, Under the condition of an ice bath, dichloromethane solution containing sulfur trioxide triethylamine compound (3.89 g, about 21.5 mmol) is dropwise added into the forsythiaside solution; stirring is performed at the same time, and the speed of the dropwise addition is 1 drop (about 50 ul/drop)/2 s, i.e., the molar ratio of the forsythiaside to the sulfur trioxide triethylamine compound in the present embodiment is 1:2.

3, After completion of the dropwise addition, under a stirring condition, temperature is raised and maintained at 110° C., and esterification reaction is carried out;

4, Under the condition of maintaining temperature at 110° C., esterification reaction is completed, upon reaction for I h, the temperature is reduced to room temperature, ammonia water (5 ml) is added to adjust the pH value to 8, the reaction mixture is subsequently distilled with a reduced pressure to remove solvent, then, sample is loaded on GF254 silica gel column chromatography, the eluent is a mixture liquid of chloroform and methanol, wherein the volumetric ratio of the chloroform to the methanol is 9:1 A forsythiaside ammonium sulfate (compound 3) is obtained by means of silica gel column chromatography.

Forsythiaside ammonium sulfate (3 g) is a white solid, which is soluble in water and ethanol. After being spread on a TLC board (with the chromatographic solution being chloroform/methanol 10: 1, and Rf being 0.4), it shows a purple-red color by spraying 10% of $H_2SO_4$-ethanol reagent. In ESI-MS spectrum, m/z[M-$NH_4$]$^-$ is 451, and the molecular weight is 469.

The $^1$H-NMR (600 MHz, $d_6$-DMSO) of compound 3 is as follows:

δ (ppm):7.4 (1H, d, J-8.4 Hz, H—), 6.9 (5H, m, Ar—H), 4,8 (1H, d, J=4.8 Hz, H-6), 4.38 (H, d, J-6,6 Hz, H-8), 4.10 (1H, d, J-9.0 Hz, H-2), 3.75 (12H, d, J=8.4 Hz, H-8,4, O—$CH_3$), 3.12 (1H, t, J=8,1Hz, H-5), 2,86 (1H, d, J-7.2 Hz, H-1);

the $^{13}$C-NMR (125 MHz, $d_6$-DMSO) of compound 3 is as follows:

δ (ppm):150.99 (C-3"), 148.97 (C-3'), 148.10 (C-4"), 142.51 (C-4'), 137.20 (C-1"), 131.73 (C-1'), 121.32 (C-5'), 118.09 (C-6'), 118.06 (C-6"), 112.09 (C-5"), 110.94 (C-2'), 110.00 (C-2"), 87.22 (C-2), 81.76 (C-6), 70.87 (C-8), 69.44 (C-4), 56.21 (C—$OCH_3$), 55.99 (C—$OCH_3$), 54.52 (C—$OCH_3$), 53.37 (C-1), 49.78 (C-5) ppm.

According to the testing data of ESI-MS, $^1$H-NMR and $^{13}$C-NMR, it is determined that the molecular formula of compound 3 is: $C_{21}H_{27}NO_9S$; and the structural formula is Embodiment 5

1, Forsythiaside (4 g, 10.75 mmol) is added into 180 ml of dried anhydrous N,N-dimethylformamide, and <stirring is carried out for dissolving, to obtain a forsythiaside solution;

2, Under the condition of an ice bath, a dichloromethane solution containing sulfur trioxide pyridinerr compound (3.68 g, about 21.5 mmol) is dropwise added into the forsythiaside solution; stirring is performed at the same time, and the speed of the dropwise addition is 1 drop (about 50 ul/drop)/2 s, i.e., the molar ratio of the forsythiaside to the sulfur trioxide pyridine compound in the present embodiment is 1:2.

3, After completion of the dropwise addition, under a stirring condition, temperature is raised and maintained at 110° C., and esterification reaction is carried out;

4, Under the condition of maintaining temperature at 110° C., esterification reaction is completed, upon reaction for 1 h, the temperature is reduced to room temperature, a methanol solution of potassium hydroxide (5 ml) is added to adjust the pH value to 8, the reaction mixture is subsequently distilled with a reduced pressure to remove solvent, then, sample is loaded on GF254 silica gel column chromatography, the eluent is a mixture liquid of chloroform sand methanol, wherein the volumetric ratio of the chloroform to the methanol is 9:1, A forsythiaside potassium sulfate (compound 2) is obtained by means of silica gel column chromatography. Forsythiaside potassium sulfate (3 g) is a white solid, which is soluble in water and ethanol. After being spread on a TLC board (with the chromatographic solution being chloroform/methanol 10:1, and Rf being 0.4), it shows a purple-red color by spraying 10% of $H_2SO_4$-ethanol reagent. In ESI-MS spectrum, m/z[M-K]$^-$ is 451, and the molecular weight is 490.

The $^1$H-NMR (600 MHz, $d_6$-DMSO) of compound 2 is as follows:

δ (ppm):7.4 (1H, d, J=8.4 Hz, H—), 6.9 (5H, m, Ar—H), 4.8 (1H, d, J-4.8 Hz, H-6), 4.38 (H, d, J=6,6 Hz, H-8), 4.10 (1H, d, J=9.0 Hz, H-2), 3.75 (12H, d, J=8:4 Hz, H-8,4, O—$CH_3$), 3.10 (1H, t, J=8.1 Hz, H-5), 2.84 (1H, d, J=7.2 Hz, H-1);

the $^{13}$C-NMR (125 MHz, $d_6$-DMSO) of compound 2 is as follows:

δ (ppm):150.99 (C-3"), 148,97 (C-3'), 148.10 (C-4"), 142.51 (C-4'), 137.20 (C-1"), 131.73 (C-1'), 121.33 (C-5'), 118.09 (C-6'), 118.06 (C-6"), 112,09 (C-5"), 110.95 (C-2'), 110.00 (C-2"), 87.23 (C-2), 81.76 (C-6), 70-87 (C-8), 69.44 (C-4), 56.21 (C—$OCH_3$), 55.99 (C—$OCH_3$), 54.52 (C—$OCH_3$), 53.37 (C-1), 49.78 (C-5) ppm.

According to the testing data of ESI-MS, 1H-NMR and $^{13}$C-NMR, it is determined that the molecular formula of compound 2 is $C_{21}H_{23}O_9SK$; the structural formula is Embodiment 6

1, Forsythiaside (4 g, 10.75 mmol) is added into into 180 ml of dried anhydrous N,N-dimethylformamide, and stirring is carried out for dissolving, to obtain a forsythiaside solution;

2, Under the condition of an ice bath, a dichloromethane solution containing sulfur trioxide thylamine compound (2.99 g, about 21.5 mmol) is dropwise added into the forsythiaside solution; stirring is performed at the same time, and the speed of the dropwise addition is 1 drop (about 50 ul/drop)/2 s, i.e., the molar ratio of the forsythiaside to the sulfur trioxide trimethylamine compound in the present embodiment is 1:2.

3, After completion of the dropwise addition, under a stirring condition, temperature is raised and maintained at 100° C., and esterification reaction is carried out;

4, Under the condition of maintaining temperature at 100° C., esterification reaction is completed, upon reaction for 1 h, the temperature is reduced to room temperature, a methanol solution of potassium hydroxide (5 ml) is added to adjust the pH value to 8, the reaction mixture is subsequently distilled with a reduced pressure to remove solvent, then, sample is loaded on GF254 silica gel column chromatography, the eluent is a mixture liquid of chloroform and methanol, wherein the volumetric ratio of the chloroform to the methanol is 9:1, A forsythiaside potassium sulfate (compound 2) is obtained by means of silica gel column chromatography. Forsythiaside potassium sulfate (3 g) is a white solid, which is soluble in water and ethanol. After being spread on a TLC board (with the chromatographic solution being chloroform/methanol 10:1, and Rf being 0.4), it shows a purple-red color by spraying 10% of $H_2SO_4$-ethanol reagent. In ESI-MS spectrum, m/z[M-K]$^-$ is 451, and the molecular weight is 490. The $^1$H-NMR (600 MHz, $d_6$-DMSO) of compound 2 is as follows:

δ (ppm):7.4 (1H, d, J=8.4 Hz, H—), 6.9 (5H, m, Ar—H), 4.8 (1H, d, J=4.8 Hz, H-6), 4.38 (H, d, J=6.6 Hz, H-8), 4.10 (1H, d, J=9.0 Hz, H-2), 3.75 (12H, d, J=8.4 Hz, H-8,4, O—$CH_3$), 3.10 (1H, t, J=8.1 Hz, H-5), 2.84 (1H, d, J=7.2 Hz, H-1);

the $^{13}$C-NMR (125 MHz, $d_6$-DMSO) of compound 2 is as follows:

δ (ppm):150.99 (C-3"), 148.97 (C-3'), 148.10 (C-4"), 142.51 (C-4'), 137.20 (C-1"), 131.73 (C-1'), 121.33 (C-5'), 118.09 (C-6'), 118.06 (C-6"). 112.09 (C-5"), 110.95 (C-2'), 110.00 (C-2"), 87.23 (C-2), 81.76 (C-6), 70.87 (C-8), 69.44 (C-4), 56.21 (C—$OCH_3$), 55.99 (C—$OCH_3$), 54.52 (C—$OCH_3$), 53.37 (C-1), 49.78 (C-5) ppm.

According to the testing data of ESI-MS, $^1$H-NMR and $^{13}$C-NMR, it is determined that the molecular formula of compound 2 is: $C_{21}H_{23}O_9SK$; the structural formula is:

Test example 1 Test of antiviral activities of forsythiaside sulfate derivatives 1 In Vitro Antiviral Test 1.1 Test Materials (1) Drugs 1) Forsythiaside sulfate derivatives: forsythiaside sodium sulfate, forsythiaside potassium sulfate and forsythiaside ammonium sulfate, which are all white powder and produced by Dalian Fusheng Natural Medicinal Development Co. Ltd., and measured respectively by two high performance liquid chromatography detectors, i.e., ultraviolet detector and evaporative light-scattering detector, through the area normalization method; and the purities thereof are 99.9%, 99.5% and 99.2% respectively.

2) Ribavirin injection, which is a colorless and transparent liquid produced by Henan Runhong Pharmaceutical Co., ltd., and the product lot number is: 1206261, and the national medicine permission, number is: H19993553; its concentration is 100 mg/ml and taken as the positive control drug in the present test.

3) Oseltamivir phosphate, which is produced by the National Institute for the Control of Pharmaceutical and Biological Products. The product lot number is: 101096-200901; The Osehamivir phosphate is taken as the positive control drug in the present test, with every injection being 100 mg.

The above-mentioned drugs are all dissolved with purified water, filtered, sterilized, subpackaged, and stored at 4° C. for standby application; all of them are drugs to be tested in the present test.

(2) Cell Strain

Cell strain of Vero cell (African, green monkey kidney cell) is preserved by College of Basic Medical Sciences of Jilin University.

(3) Virus Strains

1) Influenza virus, purchased from Virology Institute of Chinese AcademyAccademy of Preventive Medicine.

2) Parainfluenza virus, purchased from Virology Institute of Chinese Academy of Preventive Medicine.

3) Respiratory syncytial virus (RSV), purchased from Virology Institute of Chinese Academy of Preventive Medicine.

4) Coxsackievirus $B_3(CVB_3)$ strain, derived from America and preserved by the teaching and research office.

5) Coxsackievirus A16 (CoxA16) strain, given by Sendai National Hospital of Japan as a present and preserved by the teaching and research office.

6) Enterovirus EV7 I strain, given by Sendai National Hospital of Japan as a present and preserved by the teaching and research office.

7) Adenovirus (AdV), derived from pediatric laboratory of The First Hospital of Norman Bethune Health Science Center of JiLin University.

8) Herpes simplex virus type-1 HSV-1), purchased from The National Institute for the Control of Pharmaceutical and Biological Products.

(4) Main Equipment and Reagents:

| | |
|---|---|
| Biological safety cabinet | BHC-1300 II A/B3, AIRTECH |
| $CO_2$ Incubator | MCO-18AIC, SANYO |
| Inverted microscope | CKX41, OLYMPUS |
| Electronic analytical balance | AR1140/C, DHAUS |
| Culture medium | DMEM, HyClone |
| Fetal bovine serum | HyClone |
| Trypsin | Gibco |
| MTT | Sigma |
| DMSO | Tianjin Beilian Fine Chemicals Development Co., Ltd. |

1.2 Test Method (1) Preparation of Cells

Vero cell is subcultured for 1-2 d, and made into slices, the boundary line is clear; when the stereo perception and the diopter are strong, treated with trypsin, when there are needle-like wells on the cell surface, the digestive juice is absorbed completely, a few milliliters of culture broth is taken to disperse cells which are then counted and diluted with the culture broth (DMEM containing 10% of fetal bovine serum) to about $5 \times 10^7/L$, and inoculated in a 96-well culture plate until the cells are grown into a monolayer.

(2) Determination of Drug Toxicity

Cytotoxicity test: drugs are diluted according to the concentrations indicated in Table 1 for the determination of cytotoxicity.

(3) Determination of $TCID_{50}$ of Various Viruses

Various viruses are diluted by a 10-fold decrement to have different dilutions of $10^{-1}, 10^{-2}, 10^{-3}, 10^{-4}, 10^{-5}$ and $10^{-6}$, and are sequentially inoculated in the monoiayer Vero cell 96-well culture plate, 100 μL for each well, 6 wells for each dilution, and meanwhile, a normal cell control group is provided. It is incubated in 5% $CO_2$ at 37° C. for 2 h, the virus liquid is discarded, then 100 μL of cell maintenance solution is added to each well, and cultured in 5% $CO_2$ at 37° C. The cytopathic results are observed under the microscope from the 3rd day on, results are determined on the 7th-8th day and recording well, such that the highest dilution is taken as the end point where 50% of the cell wells occur a positive lesion, and the virus titer is calculated by using a karber method.

$$\mathrm{Log}TCID_{50} = XM + \frac{1}{2}d - d\frac{\sum Pi}{100} \quad \text{Formula}$$

$TCID_{50}$: 50% histocyte infection dose

XM: logarithm of the highest concentration dilution of virus d: logarithm of dilution coefficient (multiple)

Σpi: the sum of each dilution lesion percentage (4) Impact of the Drug on, the Virus-Induced Cytopathy A culture plate covered with a monolayer of cells is adopted, the culture broth is sucked and discarded, cells fare inoculated at an amount of virus attacks corresponding to

TABLE 1

Drug dilution reference table (Unit: g/L)

| | concentration gradient | | | | | | | |
|---|---|---|---|---|---|---|---|---|
| Drug | Gradient 1 | Gradient 2 | Gradient 3 | Gradient 4 | Gradient 5 | Gradient 6 | Gradient 7 | Gradient 8 |
| Forsythigenol sodium sulfate | 5 | 2.5 | 1.25 | 0.625 | 0.3125 | 0.15625 | 0.078125 | 0.039063 |
| Forsythigenol potassium sulfate | 5 | 2.5 | 1.25 | 0.625 | 0.3125 | 0.15625 | 0.078125 | 0.039063 |
| Forsythigenol ammonium sulfate | 5 | 2.5 | 1.25 | 0.625 | 0.3125 | 0.15625 | 0.078125 | 0.039063 |
| Ribavirin | 5 | 2.5 | 1.25 | 0.625 | 0.3125 | 0.15625 | 0.078125 | 0.039063 |
| Oseltamivir phosphate | 2 | 1 | 0.5 | 0.25 | 0.125 | 0.0625 | 0.03125 | 0.015625 |

The aforementioned drugs which are diluted with a maintenance solution (DMEM containing 2% or fetal bovine serum) to different concentrations are dropwise added to the Vero monolayer cell, each well is 0.2ml, there are 6 duplicate wells for each concentration, 6 wells for normal control (normal control group without adding drugs) and 6 wells for blank control (culture medium) are additionally provided, those are placed in an 5% $CO_2$ incubator at 37° C. for culturing, observing CPE with an inverted microscope every day and recording. After 72 h, 20 μL (5 mg·mL$^{-1}$) of MTT solution is added in each well, and continues to be incubated for 4 h, the culture broth in each well is sucked and discarded, 100 μL of DMSO is added in each well, and is shaken for 5 min, measuring the OD value at 492 nm to calculate cell survival rate. In SPSS 18.0 statistical software, the cell survival rate is subjected to Probit regression analysis to calculate the maximum non-toxic concentration ($TC_0$) and half toxic concentration ($TC_{50}$) of the drug on the Vero cell.

$100TCID_{50}$, and absorbed in a 5% CO ineubator at 37° C. for 2 h, various liquids with specific concentrations (about the maximum non-toxic concentration) are added, 6 duplicate wells are provided for culture as for each concentration, 200 μL/well. Ribavirin injection and oseltamivir phosphate are provided as a positive drug control group, and a normal control group (adding no virus and drug) and a virus control group (adding virus but no drug) are provided, impact of the drug on the virus-induced CPE is observed. After 72 h, the OD value is measured under 492 nm wavelength by using an MTT colorimetric method to calculate the antiviral effective rate (ER%) of the drug. In SPSS 18.0 statistical software, significant differences among the antiviral efficiencies of the various drugs are compared by using an ANOVA method.

ER%=(the average OD value in the drug treated group-the average OD value in the virus control group)/(the average OD value in the cell control group-the average OD value in the virus control group)×100%

1.3 Test Results
(1) TCID50 of Various Viruses parainfluenza virus: $\text{Log}TCID_{50} = -2 + 0.5 - \frac{100 + 100 + 50}{100} = -4$ influenza virus: $\text{Log}TCID_{50} = -2 + 0.5 - \frac{100 - 100 + 50}{100} = -4$ $CVB_3$: $\text{Log}TCID_{50} = -2 + 0.5 - \frac{100 + 100 + 100 + 50}{100} = -5$ $HSV$-1: $\text{Log}TCID_{50} = -2 + 0.5 - \frac{100 + 100 + 100 + 30}{100} = -4.8$ $AdV$: $\text{Log}TCID_{50} = -2 + 0.5 - \frac{100 + 100 + 50}{100} = -4$ $RSV$: $\text{Log}TCID_{50} = -2 + 0.5 - \frac{100 + 100 + 100 + 50}{100} = -5$ $CoxA16$: $\text{Log}TCID_{50} = -2 + 0.5 - \frac{100 + 100 + 100 + 50}{100} = -5$ $EV71$: $\text{Log}TCID_{50} = -2 + 0.5 - \frac{100 + 100 + 100 + 50}{100} = -5$ (2) Determination of Drug Toxicity
(1) Determination of Cytotoxicity of Drugs The maximum non-toxic concentrations ($TC_0$), half toxic concentrations ($TC_{50}$) of the drugs on the Vero cells and concentrations used for drug antiviral test are shown in Table 2.

TABLE 2

Drug cytotoxicity test results (unit: g/L)

| virus | forsythiaside sodium sulfate | forsythiaside potassium sulfate | forsythiaside ammonium sulfate | ribavirin | oseltamivir phosphate |
|---|---|---|---|---|---|
| the maximum non-toxic concentration | 0.128 | 0.112 | 0.105 | 0.065 | 0.28 |
| half toxic concentration | 0.685 | 0.651 | 0.555 | 1.392 | 0.832 |
| 0.30 | 0.03 | 0.03 | 0.03 | 0.70 | 0.30 |

(2) Results of Protective Effects of Drugs on the Virus-Induced Cytopathy

For the effective rates of the drugs in resisting various viruses and results of ANOVA-method one-way analysis of variance, see Table 3 for details.

TABLE 3

Statistical table of antiviral effective rates (ER %) of drugs

| virus | forsythiaside sodium sulfate | forsythiaside potassium sulfate | forsythiaside ammonium sulfate | ribavirin | oseltamivir phosphate |
|---|---|---|---|---|---|
| Influenza virus | 95.85** | 91.22** | 90.98** | 57.49** | 81.76** |
| Parainfluenza virus | 98.90** | 97.90** | 96.95** | 97.56** | 94.52** |
| CoxA16 | 100.00** | 100.00** | 100.00** | 0.70 | 2.95 |
| RSV | 85.41** | 82.41** | 81.41** | 50.08* | 37.60 |
| HSV-I | 90.82** | 88.35** | 85.51** | 62.92** | 66.56** |
| ADV | 20.91* | 17.86* | 20.88* | 0.43 | 10.31 |
| EV71 | 50.21 | 42.10 | 35.12 | 4.25** | 51.86 |
| $CVB_3$ | 10.55 | 3.50 | 7.10 | 13.44 | 1.64 |

As shown in the results of Table 3, the effective rates of forsythiasicle sulfate-forsythiaside sodium sulfate, Forsythiasicie potassium sulfate, and forsythiaside ammonium sulfate in inhibiting influenza virus, parainfluenza virus, coxsackie virus (CoxA16) are all greater than 90%, and compared with the virus control group, the differences are statistically significant; the inhibition rates for respiratory syncytial virus RSV and herpes simplex virus type-I (HSV-1) are both greater than 80%, the effective rates are both higher than 80%, and compared with the virus control group, the differences are statistically significant; and therapeutic effects of the three forsythiaside sulfate derivatives on the aforementioned viruses are superior to the trends of the ribavirin and the oseltamivir phosphate.

2, In Vivo Antiviral Test
2.1 Experimental Materials
(1) Experimental Animals

Kunming mice are provided by Norman Bethune Health Science Center of Jilin University, Medicinal animal No, 10-5219, 2) Test Reagents
Main Experimental Instruments

| Instrument name | Model | Manufacturer |
| --- | --- | --- |
| Quantitative PCR Instrument | 7300 | ABI |
| PCR Instrument | ES-60J | Shenyang Longteng Electronic Weighing Instrument Co., Ltd. |
| Electronic Analytical Balance | FA1004 | Shenyang Longteng Co., Ltd. |
| $CO_2$ Incubator | HG303-5 | Nanjing Experimental Instrument Factory |
| Super-clean Bench | SW-CJ-IF | Suzhou Antai Air Tech Co., Ltd. |
| Inverted microscope | CKX41 | Olympus Instrument |
| $-80°$ C. ultra-low temperature freezer | TECON-5082 | Australia |
| Water bath oscillator | HZS-H | Harbin Donglian Co., Ltd. |
| Microplate reader | TECAN A-5082 | Australia |
| Spectrophotometer | 7550 model | Japan |

2.2 Experimental Method (1) Determination of the median lethal dose of mice due to influenza virus and parainfluenza virus The influenza virus and parainfluenza virus (cell lysate) are diluted by a 10-fold decrement into virus liquids with concentrations of $10^{-1}$, $10^{-2}$, $10^{-3}$, $10^{-4}$ and $10^{-5}$. 120 Kunming mice are obtained, 60 of which are provided for the influenza virus group and the remaining 60 are provided for the parainfluenza virus group, and are randomly divided into 6 groups separately; The mice are lightly anesthetized with ether, and are infected nasally with virus liquids having different dilutions at 0.03 mL/mouse. Meanwhile blank control is sets and the virus liquids is replaced with saline. Death and survival are regarded as the observational indexes, observation is performed every day for 14 days after infection. Those died within 24 h of infection are nonspecific death and are not counted up, the virus liquid $LD_{50}$ is calculated by using a Karber method. The calculation formula is:

$$LogLD_{50} = XM + \frac{1}{2}d - d\frac{\sum Pi}{100}$$

[wherein: $LD_{50}$ is the median lethal dose; XM is the logarithm of the highest concentration dilution of virus: d is the logarithm of the dilution coefficient (multiple); and $\Sigma pi$ is the sum of each dilution lesion percentage].

(2) Research on Forsythiaside Sulfate on Resistance to Pneumonia Caused by Anti-Influenza Virus and Parainfluenza Virus Infection 1) Experimental Animals and Groups 360 four weeks old mice are adopted to perform two tests. 180 mice are adopted and randomly divided into 18 groups (10 for each group) for test of determining lung index and lung index inhibition rate of forsythiaside sulfate to the mice infected by the influenza virus. The remaining 180 mice are adopted and randomly divided into 18 groups (10 for each group) for a test of determining lung suspension virus hemagglutination titer of forsythiaside sulfate.

2) Infection Method

A degreasing cotton is placed in a 200-300 mL beaker, in which a suitable amount of ether (just for making cotton wet) is added, the beaker containing the degreasing cotton is inverted upside down, the mice are extremely excited when anesthetized therein, and are made to lie on their backs when clearly weak, the mice are infected nasally with $15LD_{50}$ influenza virus a .d parainfluenza virus at 0.03 ml/nostril, and the virus suspension is replaced with normal saline in the normal control group.

3) Administration Method and Administration Dosage

Conventional intragastric administration is carried out respectively for forsythiaside sodium sulfate and forsythiaside potassium sulfate drug groups and ribavirin control group one day before infection. The high, medium and low administration dosages of the forsythiaside sodium sulfate and forsythiaside potassium sulfate are 13.0 mg/kg, 6.5 mg/kg and 3.25 mg/kg respectively, and the administration dosage of ribavirin positive drug is 58.5 mg/kg. The administration is performed once a day for five consecutive days. The virus control group is drenched with normal saline of the same volume.

4) Observational Index

① Lung Index Determination

In the fifth day after drugs are administered by mice, the mice are inhibited from drinking water for 8 hours first; then, after the mice are weighed, their eyes are moved and said animals are killed by bleeding; their chest cavities are opened to take out total lungs, which are washed using normal saline twice, and sucking up the moisture on the surfaces of the lungs by using filter paper; then the lungs are weighed by using an electronic balance, and the lung index and the lung index inhibition rate are calculated according to the following equations:

lung index=(mice lung weight/mice weight)×100%;

lung index inhibition rate=(average lung index of infection model group−average lung index of experimental group)/average lung index of infection model group×100%.

② Determination of Lung Suspension Virus Hemagglutination Titer

Various groups of mice lungs are respectively taken in the fifth day after treatment, and are ground into homogenate by a homogenizer at a low temperature; the homogenate is diluted into 10% of lung tissue suspension with normal saline; centrifugation is performed to obtain a supernatant, which is double diluted and dripped to a titration plate with 0.2 ml/well; 0.2 ml of 1% chicken erythrocyte suspension is added into each hole and mixed well; the titration plate is placed in a room-temperature environment for 30 minutes to observe and record hemagglutination titers. The end point appears when erythrocyte is agglutinated to be (++), and its titer is expressed by the suspension dilution multiple.

③ Observation of Lung Histomorphology

Various mice lungs are respectively taken in the fifth day after treatment; general pathological changes of their viscera are observed by naked eyes and are recorded. The lungs are cleaned by rinsing with normal saline and moisture thereon is sucked up by using filter paper; a portion of the lung is fixed with 10% formaldehyde, paraffin-embedded, sliced and HE-strained; observation and photographing are performed under a microscope.

2.3 Experimental Results and Analysis (1) Determination Result of the Median Lethal Dose of Mice Due to Influenza Virus and Parainfluenza Virus Kunming mice in the experiment groups are respectively infected nasally with 30 μL of influenza virus and parainfluenza virus liquids of different concentrations; in the third day of infection, all of the mice in the first three groups ($10^{-1}$ group, $10^{-2}$ group and $10^{-3}$ group based on virus concentrations) experience disease symptoms of different degrees: pilotnotor fur, trembling, decreased appetite and so on; in the fifth day, the mice stumble; in the sixth day, the mice in the group of the highest virus concentration begin to die, and death occurs successively in the remaining groups in the seventh day after infection. After the observation of 14 days is complete, the mortality of mice of each group is counted, the results of which are shown in Tables 3 and 4. By calculation, $LD_{50}$ of the influenza virus is a dilution $10^{-2.9}$, and $LD_{50}$ of the parainfluenza virus is a dilution $10^{-2.5}$.

TABLE 3

Statistics of test results of median lethal dose of influenza virus

| Influenza virus group | Cumulative mortality | Cumulative survival | Cumulative mortality rate |
|---|---|---|---|
| $10^{-1}$ group | 9 | 1 | 90% |
| $10^{-2}$ group | 7 | 3 | 70% |
| $10^{-3}$ group | 4 | 6 | 40% |
| $10^{-4}$ group | 3 | 7 | 30% |
| $10^{-5}$ group | 1 | 9 | 10% |
| Blank group | 0 | 10 | 0% |

$LD_{50}$ of the virus is calculated by using a Karber method. $LogLD_{50}$ of influenza virus is as follows:

$$LogLD_{50} = XM + \frac{1}{2}d - d\frac{\sum Pi}{100} =$$
$$-1 + 0.5 - (80\% + 60\% + 40\% + 20\% + 0\% + 0\%) = -2.9$$

TABLE 4

Statistics of test results of median lethal dose of parainfluenza virus

| Parainfluenza virus group | Cumulative mortality | Cumulative survival | Cumulative mortality rate |
|---|---|---|---|
| $10^{-1}$ group | 8 | 2 | 80% |
| $10^{-2}$ group | 6 | 4 | 60% |
| $10^{-3}$ group | 4 | 6 | 40% |
| $10^{-4}$ group | 2 | 8 | 20% |
| $10^{-5}$ group | 0 | 10 | 0% |
| Blank group | 0 | 10 | 0% |

LD50 of the virus is calculated by using a Karher method. LogLD50 of parainfluenza virus is as follows:

$$LogLD_{50} = XM + \frac{1}{2}d - d\frac{\sum Pi}{100} =$$
$$-1 + 0.5 - (90\% + 70\% + 40\% + 30\% + 10\% + 0\%) = -2.5$$

(2) Results of Effects of Forsythiaside Sulfate on Resistance to Pneumonia Caused by Influenza Virus and Parainfluenza Virus Infections ① Lung Index Determination After mice are infected with influenza virus and parainfluenza virus, the average lung index result shows that: compared with the infection model group, the lung indexes of the normal control group, the drug groups with various concentrations and the ribavirin group decrease significantly (P<0.05); when the concentration of forsythiaside sulfate is within the range from 3.25 to 13.0 mg/kg/d, a certain protective effect is achieved, and all lung indexes decrease significantly; although the decrease in the high dosage group of forsythiaside sulfate is more significant when compared with other two groups, there are no significant differences among various groups upon comparison (P>0.05). The medium and high dosage groups of forsythiaside sulfate are superior to the ribavirin group (P>0.05). For results, see Fables 5 and 6.

TABLE 5

Impact of forsythiaside sulfate on the lung index of influenza virus infected mice and the lung index inhibition rate

| Groups | Number of animals | Drug dosage (mg/kg/d) | Lung index ($\overline{X} \pm S$) | Lung index inhibition rate (%) | P value | P value |
|---|---|---|---|---|---|---|
| Normal control group | 10 | 0 | 1.274 ± 0.107 | — | *<0.05 | #>0.05 |
| Virus control group | 10 | 0 | 1.488 ± 0.088 | — | *<0.05 | #<0.05 |
| Ribavirin group | 10 | 58.5 | 1.282 ± .064 | 13.84 | | |
| Forsythiaside sodium sulfate high dosage group | 10 | 13.0 | 1.1809 ± .057 | 20.73 | *<0.05 | #>0.05 |
| Forsythiaside sodium sulfate medium dosage group | 10 | 6.5 | 1.264 ± 0.051 | 15.03 | *<0.05 | #>0.05 |
| Forsythiaside sodium sulfate low dosage group | 10 | 3.25 | 1.344 ± 0.035 | 9.69 | *<0.05 | #>0.05 |

TABLE 5-continued

Impact of forsythiaside sulfate on the lung index of influenza virus infected mice and the lung index inhibition rate

| Groups | Number of animals | Drug dosage (mg/kg/d) | Lung index ($\bar{X} \pm S$) | Lung index inhibition rate (%) | P value | P value |
|---|---|---|---|---|---|---|
| Forsythiaside potassium sulfate high dosage group | 10 | 13.0 | 1.190 ± 0.061 | 20.03 | *<0.05 | #>0.05 |
| Forsythiaside potassium sulfate medium dosage group | 10 | 6.5 | 1.262 ± 0.058 | 15.22 | *<0.05 | #>0.05 |
| Forsythiaside potassium sulfate low dosage group | 10 | 3.25 | 1.343 ± 0.044 | 9.77 | *<0.05 | #>0.05 |

*represents comparison with the virus control group;
represents comparison with the ribavirin group

TABLE 6 impact of forsythiaside sulfate on the lung index of parainfluenza virus infected mice and the lung index inhibition rate

| Groups | Number of animals | drug dose (mg/kg/d) | Lung index ($\bar{X} \pm S$) | Lung index inhibition rate (%) | P value | P value |
|---|---|---|---|---|---|---|
| Normal control group | 10 | 0 | 1.312 ± 0.046 | — | *<0.05 | #>0.05 |
| Virus control group | 10 | 0 | 1.598 ± 0.071 | — | *<0.05 | #<0.05 |
| Ribavirin group | 10 | 58.5 | 1.392 ± 0.070 | 12.89 | | |
| Forsythiaside sodium sulfate high dosage group | 10 | 13.0 | 1.331 ± 0.073 | 16.73 | *<0.05 | #>0.05 |
| Forsythiaside sodium sulfate medium dosage group | 10 | 6.5 | 1.303 ± 0.062 | 18.46 | *<0.05 | #>0.05 |
| Forsythiaside sodium sulfate low dosage group | 10 | 3.25 | 1.311 ± 0.049 | 17.96 | *<0.05 | #>0.05 |
| Forsythiaside potassium sulfate high dosage group | 10 | 13.0 | 1.308 ± 0.085 | 18.13 | *<0.05 | #>0.05 |
| Forsythiaside potassium sulfate medium dosage group | 10 | 6.5 | 1.286 ± 0.078 | 19.55 | *<0.05 | #>0.05 |
| Forsythiaside potassium sulfate low dosage group | 10 | 3.25 | 1.259 ± 0.041 | 17.10 | *<0.05 | #>0.05 |

*represents comparison with the virus control group;
represents comparison with the ribavirin group ② Determination of Lung Suspension Virus Hemagglutination Titer After mice are infected with the influenza virus and parainfluenza virus, the lung tissue hemagglutination titers (InX) of the infection model group are respectively 32.33 and 33.86, after treatment with forsythiaside sulfate of different concentranons for 5 days, the lung tissue virus hemagglutination titers both decrease to some extent; as compared with the infection model group, the difference is significant, (P<0.05). As compared with the ribavirin group, the virus hemagglutination titers of the high, medium, and low dosage groups of forsythiaside sulfate are all higher than that of the ribavirin group, the differences are significant (P<0.05); upon comparison, the hemagglutination titer of the high dosage group of forsythiaside sulfate is significantly different from those of the other two groups (P<0.05), as shown in Table 10, Upon comparison, there is no significant difference between the high dosage group of forsythiaside sulfate and the ribavirin group of the parainfluenza virus infected mice (P>0.05), the medium and low dosage groups of forsythiaside sulfate are both superior to the ribavirin group, the differences are significant (P<0.05); upon comparison, the hemagglutination titer of the high dosage group of forsythiaside sulfate is significantly different from that of the low dosage group of forsythiaside sulfate (P>0.05), as shown in Tables 7 and 8.

TABLE 7

Impact of forsythiaside sulfate on the lung suspension hemagglutination titer of the influenza virus infected mice

| Groups | Number of animals | Drug dose (mg/kg/d) | Hemagglutination titer (InX) | P value | P value |
|---|---|---|---|---|---|
| Normal control group | 10 | 0 | 0 | *<0.05 | *<0.05 |
| Virus control group | 10 | 0 | 32.33 ± 1.187 | | #<0.05 |
| Ribavirin group | 10 | 58.5 | 21.13 ± 0.986 | *<0.05 | |
| Forsythiaside sodium sulfate high dosage group | 10 | 13.0 | 20.07 ± 0.646 | *<0.05 | #<0.05 |
| Forsythiaside sodium sulfate medium dosage group | 10 | 6.5 | 21.29 ± 0.504 | *<0.05 | #<0.05 |
| Forsythiaside sodium sulfate low dosage group | 10 | 3.25 | 23.93 ± 1.392 | *<0.05 | #<0.05 |
| Forsythiaside potassium sulfate high dosage group | 10 | 13.0 | 19.95 ± 0.595 | *<0.05 | #<0.05 |
| Forsythiaside potassium sulfate medium dosage group | 10 | 6.5 | 21.06 ± 0.515 | *<0.05 | #<0.05 |
| Forsythiaside potassium sulfate low dosage group | 10 | 3.25 | 22.11 ± 1.012 | *<0.05 | #<0.05 |

*represents comparison with the virus control group;
represents comparison with the ribavirin group

TABLE 8

Impact of forsythiaside sulfate on the lung suspension hemagglutination titer of the parainfluenza virus infected mice

| Groups | Number of animals | Drug dose (mg/kg/d) | Hemagglutination titer (InX) | P value | P value |
|---|---|---|---|---|---|
| Normal control group | 10 | 0 | 0 | *<0.05 | *<0.05 |
| Virus control group | 10 | 0 | 33.86 ± 1.264 | | #<0.05 |
| Ribavirin group | 10 | 58.5 | 26.73 ± 1.193 | *<0.05 | |
| Forsythiaside sodium sulfate high dosage group | 10 | 13.0 | 19.82 ± 0.981 | *<0.05 | #>0.05 |
| Forsythiaside sodium sulfate medium dosage group | 10 | 6.5 | 21.01 ± 0.614 | *<0.05 | #<0.05 |
| Forsythiaside sodium sulfate low dosage group | 10 | 3.25 | 23.26 ± 0.991 | *<0.05 | #<0.05 |
| Forsythiaside potassium sulfate high dosage group | 10 | 13.0 | 20.91 ± 0.825 | *<0.05 | #>0.05 |
| Forsythiaside potassium sulfate medium dosage group | 10 | 65 | 22.05 ± 0.829 | *<0.05 | #<0.05 |
| Forsythiaside potassium sulfate low dosage group | 10 | 3.25 | 23.88 ± 0.953 | *<0.05 | #<0.05 |

*represents comparison with the virus control group;
represents comparison with the ribavirin group ③ Detection Results of Lung Histology The lungs of the mice in the influenza virus and parainfluenza virus pneumonia model group are mostly congested, suffered from edema lesion; some the lung turn out to be consolidation areas with dark brown appearance, the seriously affected ones appear brownish red hemorrhagic focuses. Microscopically, it can be seen that the interstitial lung, such as bronchi, bronchioles and alveolar walls, are suffered from congestion, edema and lymphocytes, mononuclear cell infiltration. alveolar wall widening, and inflammatory reaction of pulmonary alveoli. After the influenza virus and parainfluenza virus pneumonia mice models are treated with the forsythiaside sulfate, the general pathological changes of the lungs of each group of mice are significantly reduced, and some of the lung tissues are normal in shape and structure; compared with the infection model group, the alveolar septum is thinner, the infiltration number of the mononuclear cells of the alveolar wall and bronchiole wall is less, there is no leakage in the cavity, and the lesions are significantly reduced. As compared with the infection model group, the medium and high dosage groups of the forsythiaside sulfate in treating parainfluenza virus pneumonia have significantly thinner alveolar septum, less infiltration number of mononuclear cells, no leakage in the cavity, and significantly reduced lesions.

Figure 1:
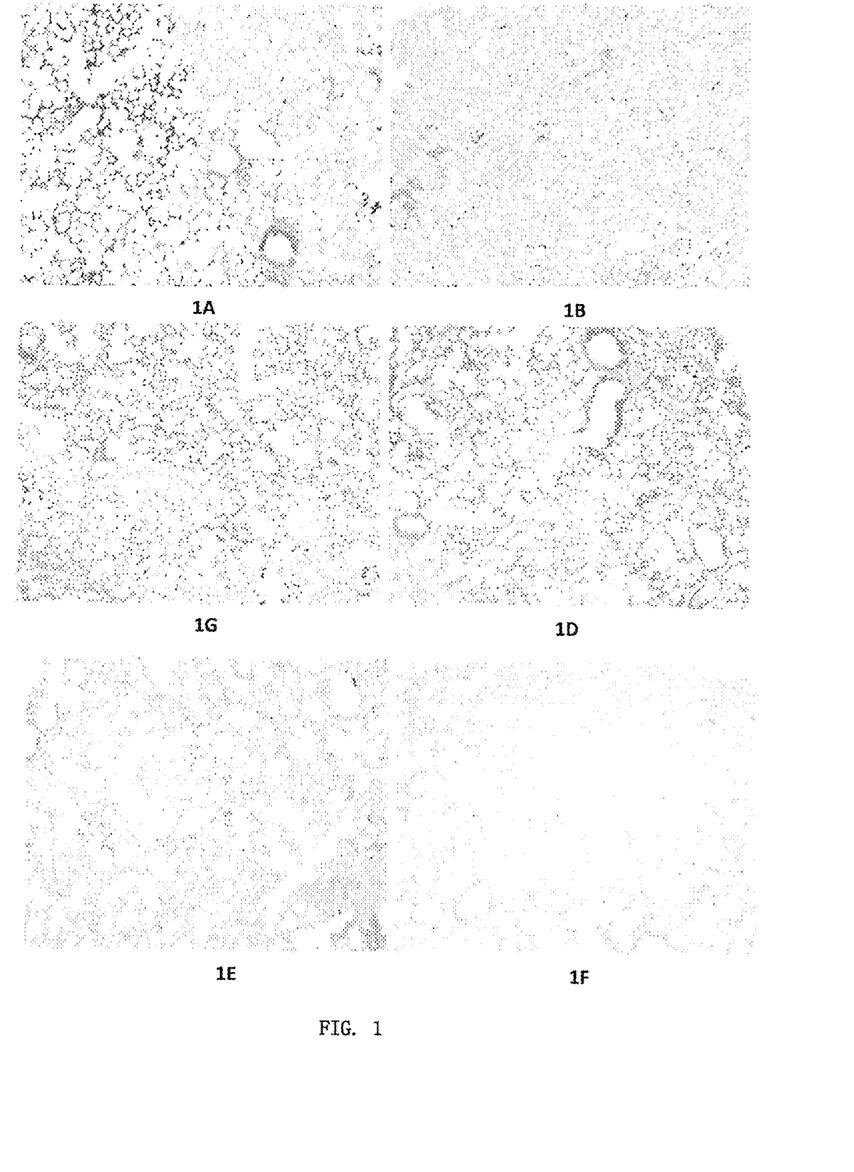
FIG. 1 is a microscopic examination image of influenza virus pneumonia model mice pulmonary tissue pathological section.

The mouse lung tissue pathological slice microscopic examination results of the influenza virus pneumonia model are shown in FIG. 1; FIG. 1A shows the lung tissue of a normal mouse; FIG. 1B shows the lung tissue of an influenza virus pneumonia, mouse; FIG. 1C shows the lung tissue of the mouse of the influenza virus pneumonia mouse model after being treated with positive drug ribavirin; FIG. 1D shows the lung tissue of the mouse of the influenza virus pneumonia mouse model after being treated with high-dosage forsythiaside sulfate; FIG. 1E shows the lung tissue of the mouse of the influenza virus pneumonia mouse model after being treated with medium-dosage forsythiaside sulfate; FIG. 1F shows the lung tissue of the mouse of the influenza virus pneumonia mouse model after being treated with low-dosage forsythiaside sulfate.

Figure 2:
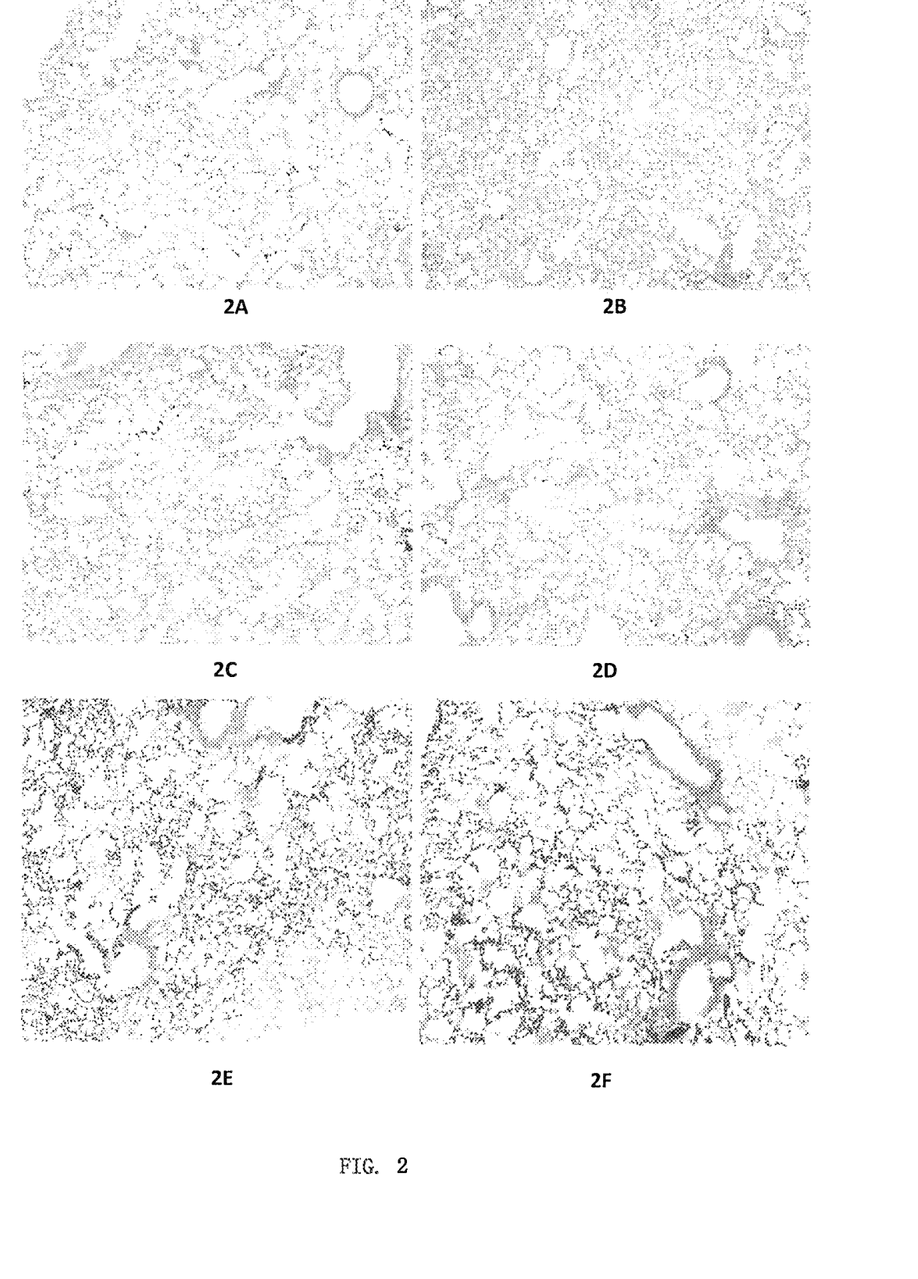
FIG. 2 is a microscopic examination image of parainfluenza virus pneumonia model mice pulmonary tissue pathological section.

The mouse lung tissue pathological slice microscopic examination results of the parainfluenza virus pneumonia model are shown in FIG. 2; FIG. 2A shows :he lung tissue of a normal mouse; FIG. 2B shows the lung tissue of a pariiintluenza virus pneumonia mouse; FIG. 2C shows the lung tissue of the mouse of the parainfluenza virus pneumonia mouse model after being treated with positive drug ribavirin; FIG. 2D shows the lung tissue of the mouse of the influenza virus pneumonia mouse model after being treated with high-dosage forsythiaside sulfate; FIG. 2E shows the lung tissue of the mouse of the parainfluenza virus pneumonia mouse model after being treated with medium-dosage forsythiaside sulfate; FIG. 2F shows the lung tissue of the mouse of the parainfluenza virus pneumonia mouse model after being treated with low-dosage thrsythiaside sulfate.

2.4 Conclusions

In vivo antiviral test results show that the forsythiaside sulfates (forsythiaside sodium sulfate and forsythiaside potassium sulfate) have relatively signifciant inhibition effects on influenza virus and parainfluenza virus as well as the mice viral pneumonia caused thereby at a dosage range of 3.25 mg/kg/d to 13 mg/kg/d, can significantly reduce the lung index and hemaggiutination titer thereof, also significantly improve the pulmonary tissue pathology, and have significant difference as compared with the model control group.

The invention claimed is:

1. A forsythiaside sulfate as represented by the following chemical structural formula, wherein R is H, Na$^+$, K$^+$, NH$_4$$^+$, tetramethyl ammonium, tetraethyl ammonium, methyl amino, dimethylamino, trimethylamino, triethylamino, diethylamino, ethylamino, ethanolamino, diethanolamino, piperidyl, piperazinyl or pyrazinyl.

2. A preparation method of the forsythiaside sulfate thereof according to claim 1, comprising the following sequentially performed steps:
  1) dissolving forsythiaside in an organic solvent to obtain a forsythiaside solution;
  2) first adding a sulfating agent into the forsythiaside solution and mixing well; and then, carrying out an esterification reaction to obtain a product mixture liquid;
  3) adding a base to adjust the pH value of the mixture liquid to 8-10; and
  4) separating and purifying the mixture liquid to obtain the final product.

3. The preparation method according to claim 2, wherein the sulfating agent in step 2) is selected from the group consisting of chlorosulfonic acid, sulfur trioxide-triethylamine complex, sulfur trioxide-pyridine complex and sulfur trioxide-trimethylamine complex.

4. The preparation method according to claim 2, wherein the base in step 3) is selected from the group consisting of an organic base and inorganic base.

5. The preparation method according to claim 2, wherein the organic solvent in step 1) is selected from the group consisting of pyridine, N,N-dimethylformamide, N, N-dimethylacetamide and dichloromethane.

6. The preparation method according to claim 2, wherein the sulfating agent is added in the forsythiaside solution at a temperature of 0-5° C. in step 2).

7. The preparation method according to claim 2, wherein a molar ratio of the forsythiaside in the forsythiaside solution to the sulfating agent in step 2) is 1:1-10.

8. A method of treating virosis in a subject, comprising administrating to the subject a therapeutically effective amount of an antiviral drug comprising the forsythiaside sulfate according to claim 1.

9. The method according to claim 8, wherein the antiviral drug is selected from the group consisting of anti-influenza drugs, anti-parainfluenza drugs, anti-respiratory syncytial virus drugs, anti-herpes simplex virus type-I drugs, anti-coxsackievirus A16 drugs, and any combination thereof.

10. An antiviral drug, comprising a forsythiaside sulfate according to claim 1.

* * * * *